United States Patent
Schaefer

(10) Patent No.: US 7,458,117 B2
(45) Date of Patent: Dec. 2, 2008

(54) PROTECTIVE COVER AND PATIENT SECURITY APPARATUS

(75) Inventor: John W. Schaefer, Burton, MI (US)

(73) Assignee: Contour fabricators, Inc., Fenton, MI (US)

( * ) Notice: Subject to any disclaimer, the term of this patent is extended or adjusted under 35 U.S.C. 154(b) by 38 days.

(21) Appl. No.: 11/022,101

(22) Filed: Dec. 23, 2004

(65) Prior Publication Data

US 2006/0137095 A1    Jun. 29, 2006

(51) Int. Cl.
*A47G 9/02* (2006.01)
*A47C 31/10* (2006.01)
*A47G 9/00* (2006.01)

(52) U.S. Cl. .................................. 5/495; 5/482; 5/502

(58) Field of Classification Search .................. 5/606, 5/484, 487, 496, 498, 482, 486, 502, 500
See application file for complete search history.

(56) References Cited

U.S. PATENT DOCUMENTS

| | | | |
|---|---|---|---|
| 596,842 A * | 1/1898 | Borwell ...................... 428/221 |
| 1,334,901 A | 3/1920 | Higdon |
| 2,591,082 A * | 4/1952 | Lynch ............................ 5/606 |
| 2,787,794 A * | 4/1957 | Hughes et al. ................ 5/496 |
| 2,804,632 A * | 9/1957 | Ford .............................. 5/496 |
| 3,083,379 A * | 4/1963 | Marinsky ....................... 5/496 |
| 3,413,665 A * | 12/1968 | Amet ............................ 5/496 |
| 3,490,443 A * | 1/1970 | Decupper .................... 601/11 |
| 3,601,824 A * | 8/1971 | Bradford ....................... 5/628 |
| 3,924,281 A * | 12/1975 | Gibbs ........................... 5/88.1 |
| 4,357,722 A * | 11/1982 | Thompson .................... 5/606 |
| 4,389,744 A * | 6/1983 | Monroe ......................... 5/498 |
| 4,650,171 A * | 3/1987 | Howorth ....................... 5/600 |
| 4,723,331 A * | 2/1988 | Weiss ............................ 5/497 |
| 4,843,665 A * | 7/1989 | Cockel et al. ................ 5/88.1 |
| 4,945,585 A * | 8/1990 | Stewart ......................... 5/122 |
| 4,964,184 A * | 10/1990 | Lewis ............................ 5/496 |
| 4,979,251 A * | 12/1990 | Lazar ............................ 5/496 |
| 5,072,470 A * | 12/1991 | Lysiak ........................... 5/496 |
| 5,101,527 A * | 4/1992 | Wadsworth et al. .......... 5/727 |
| 5,103,511 A * | 4/1992 | Sequin .......................... 5/607 |
| 5,148,558 A * | 9/1992 | Dunn ....................... 5/81.1 T |
| 5,208,926 A * | 5/1993 | Stackhouse ................... 5/482 |
| 5,557,814 A * | 9/1996 | Cybulski ....................... 5/496 |
| 5,575,025 A | 11/1996 | Peters |
| 5,615,425 A | 4/1997 | Corente |
| 5,749,112 A | 5/1998 | Metzler |
| 6,061,851 A * | 5/2000 | Crowell ......................... 5/497 |

(Continued)

FOREIGN PATENT DOCUMENTS

FR    92 05160    4/1992

*Primary Examiner*—Patricia Engle
*Assistant Examiner*—Jonathan J Liu
(74) *Attorney, Agent, or Firm*—John K. McCulloch

(57) ABSTRACT

A sheet assembly adapted to occupy a position beneath a patient and an upper surface of a patient support. The assembly has overlying upper and lower pliable sheets formed of a material of low density gradient and having central sections from which upper and lower flaps extend laterally. The lower flaps may be secured to the patient support and the upper flaps may be elevated to and maintained at a level above that of the upper surface of the patient support, thereby providing a safeguard against the patient's falling off the support surface.

9 Claims, 4 Drawing Sheets

U.S. PATENT DOCUMENTS

| | | | |
|---|---|---|---|
| 6,108,836 A * | 8/2000 | Keene, III | 5/497 |
| 6,122,781 A * | 9/2000 | Stephenson | 5/482 |
| 6,453,492 B1 | 9/2002 | Sturrock | |
| 6,467,106 B1 | 10/2002 | Heimbrock | |
| 6,481,736 B1 * | 11/2002 | Chan | 280/288.4 |
| 6,560,797 B2 * | 5/2003 | Maturaporn | 5/482 |
| 6,637,054 B2 * | 10/2003 | Chuang | 5/502 |
| 6,678,906 B1 * | 1/2004 | Thompson | 5/502 |
| 6,725,477 B2 * | 4/2004 | Ciaglia et al. | 5/497 |
| 6,799,341 B2 * | 10/2004 | Wootten, Jr. | 5/497 |
| 6,823,544 B2 * | 11/2004 | Treece | 5/497 |
| 6,857,146 B2 * | 2/2005 | Landry | 5/494 |
| 7,047,580 B2 * | 5/2006 | Finn | 5/502 |
| 7,051,388 B1 * | 5/2006 | Taddeo | 5/498 |
| 7,082,631 B2 * | 8/2006 | Czop | 5/484 |
| 2003/0070226 A1 | 4/2003 | Heimbrock | |

* cited by examiner

PROTECTIVE COVER AND PATIENT SECURITY APPARATUS

This invention relates to apparatus for underlying a patient on a support surface to protect such surface and restraining such patient from falling off the surface.

BACKGROUND OF THE INVENTION

Patient supports for use in performing X-ray or other imaging procedures conventionally are provided with casters and other features enabling them to serve as gurneys or trolleys for supporting and transporting a patient. Normally, it is desirable to provide such supports with patient security means for preventing a patient from falling or sliding off the support while imaging procedures are being performed or during transport of the patient. In general medical imaging applications patient security often is provided by means of strapping systems. However, in emergency medicine procedures strapping cannot always be used because such strapping applies mechanical loads to the patient that may not be suitable for a patient having fractures or other injuries. Strapping also may interfere with the immediate access to open wounds and, occasionally, may not be usable because of foreign objects embedded in or projecting from the patient's body. Thus, patient security for gurneys and trolleys traditionally has been accomplished by means of adjustable side rails.

Most side rails are rigid structures and often have been made of tubular steel or aluminum members consisting of one or more lengthwise components and two or more vertical components. Such structures conventionally have gaps of several inches between the lengthwise components and several feet between the vertical components. When side rails of these kinds are provided on a medical imaging support which also serves as a gurney or trolley, such side rails interfere with imaging in the lateral and oblique directions because of the radiolucent opacity of metals and the artifact-causing abrupt density transition at the metal/air boundaries. Even though such side rails may be made of carbon fiber composites to improve their radiolucency, the additional cost of such materials is substantial. Further, even though radiolucency may be improved by the use of such composite materials, such structures have abrupt density transitions at the solid-to-air boundaries.

Another shortcoming of the use of rails of tube-like construction is that the gaps between and under the lengthwise tubes allow parts of the patient's body to project beyond the plane of a side rail. This may allow those body parts to extend into pinch points and danger zones associated with adjacent medical imaging equipment, or otherwise create injury-prone situations. This is of particular concern in emergency medicine venues where the patient may not be able to cooperate with medical personnel by remaining stationary.

Some composite rails have been made as solid walls or plates. This is a less expensive topology to manufacture and it has a fairly consistent radiologic density. However, any such rail arrangement must have a means of installation and removal so as to permit patient loading and unloading, or sometimes access to a patient by medical personnel during emergency situations. Because it is desirable that lateral imaging be artifact-free from the tabletop upward to a specified height in order to be able to image the patient's entire body, solid plate rail structures generally must meet a table surface without any gaps therebetween. These requirements for removability and gap free mounting can be especially troublesome in meeting the need for haste in the installation of such rails inasmuch as some portions of the patient's body may not be clear at the installation zone, thereby creating a pinch point situation when a solid plate rail is moved into its installed position.

Another problem encountered with removable, rigid side rails is that they present a physical location challenge when they are not in their installed position. If such rails are fully removable they tend to be set aside and left behind when a patient trolley or gurney is moved, thereby disrupting subsequent usage of the trolley or gurney until the missing side rails are retrieved.

If a side rail is hinged or otherwise mounted to the support so as to swing outward and downward to a storage position below the support top, the raising and lowering of such a side rail may be impossible while the trolley or gurney is located closely alongside another patient support, such as a stretcher or a surgical table, to which a patient must be moved for further treatment. Such downward storage positions also may interfere with the close passage of medical imaging equipment under the support top, inasmuch as such imaging equipment often must be provided with a clearance below the support top for medically acceptable imaging precision.

If such rails are mounted so as to swing downward into a pocket in or below the support top, or are otherwise designed to be lowered without taking up any space either below or beyond the top, the pocket in the support inevitably causes the top to have an inconsistent radiolucent density across its area which creates artifacting for anterior-posterior imaging. Such pocket designs also may involve an unacceptable compromise of structural strength, particularly in view of the necessity of making support tops increasingly stronger to support increasingly heavier patient populations while still maximizing such tops' radiolucency characteristics.

A related disadvantage of rigid side rails of all types is that their removal, storage, and reinstallation require so much time that patient survival may be compromised, especially in emergency medicine situations.

Another problem with rigid side rails of all types that are fully removable is that they may not be safe for use on gurneys or trolleys for reception of patients from a helicopter. The main rotor blades of a helicopter commonly are spinning while a patient is transferred from the helicopter stretcher to the patient gurney or trolley. Consequently, if a rigid side rail should inadvertently be raised into the path of movement of a rotor blade, a catastrophe could occur.

A still further problem with rigid side rails of all types, and particularly those used in emergency medicine situations, is that their rigid nature can interfere with the positioning of certain patients who must be imaged while being equipped with devices such as emergency splints or backboards which, even though they need not be imaged themselves, may project beyond the boundaries of the patient's body to such an extent that the side rails cannot be installed when the patient is optimally positioned.

Quite apart from the foregoing undesirable characteristics of currently available patient security apparatus such apparatus presents problems in coping with contamination prevention, cleaning, and physical damage. It is well known that general medical imaging tables accumulate biological contamination in film or solid form from normal contact with patients' skin, hair, and clothing and must be cleaned periodically. This problem is much more acute in connection with medical imaging tables utilized in emergency medicine where it may be desirable to image patients before the release of biological fluids can be resolved or prevented and where a patient's garments or body may be contaminated prior to the arrival at the treatment site. At times, large quantities of blood and other fluids can contaminate the area around an emergency medicine patient during the initial period of treatment. If such fluids are not captured close to the patient, they may run off the table and contaminate lower parts of the gurney or trolley, associated medical imaging equipment, or the floor under such equipment. In addition, emergency medicine patients also sometimes arrive at a treatment site with foreign objects or broken bones projecting from their bodies in such manner as to present cutting or puncturing hazards to any vulnerable equipment at the site.

A principal object of the invention is to provide a protective covering for a patient support and patient security apparatus which overcomes or greatly minimizes the objectionable characteristics referred to above.

SUMMARY OF THE INVENTION

Apparatus constructed in accordance with the preferred embodiment of the invention comprises upper and lower pliable sheets of waterproof material adapted to be placed on the upper surface of a patient support in a position between the upper surface of the support and a patient. The support may be a gurney, a trolley, a medical imaging table, or any other kind of appropriate equipment. The width of the lower sheet is greater than that of the support surface, thereby enabling the lower sheet to have two flaps, one at each side of the support surface, which may be turned under the edges of the support surface and secured thereto. The upper sheet has appropriate length and width dimensions and is wider than the lower sheet so that patient restraining flaps are formed at each of the two opposite sides of the upper sheet. At the free edge of each restraining flap is a hem which forms a pocket for the accommodation of an elongate retaining rod having an enlargement at each of its opposite ends.

At opposite ends of the support table is a pair of upstanding anchor bars having slotted free ends for the removable accommodation of the retainer rod. Either of the restraining flaps may be raised relative to the support surface and maintained in an elevated position by inserting the opposite ends of the associated retaining rod in the slots of the anchor bars. The length of the upper sheet is sufficiently great that the raising of the restraining flaps to their elevated positions causes the edges at opposite ends of the upper sheet to be raised upwardly, thereby providing a retaining wall at each end of that part of the upper sheet overlying the support table for the purpose of preventing the escape of fluids from opposite ends of such sheet.

All of the materials used in forming the protective sheet construction are such that they have little or no adverse effect on imaging procedures. The materials from which the sheets are formed are of sufficient thickness and strength as to provide security against a patient's falling off the support surface. Such materials are of consistent composition and of substantially uniform thickness so as to have little or no density gradients. Such materials also are waterproof and easily and thoroughly cleanable.

THE DRAWINGS

A sheet assembly constructed in accordance with the presently preferred embodiment of the invention is illustrated in the accompanying drawings wherein.

THE PREFERRED EMBODIMENT

Figure 1:
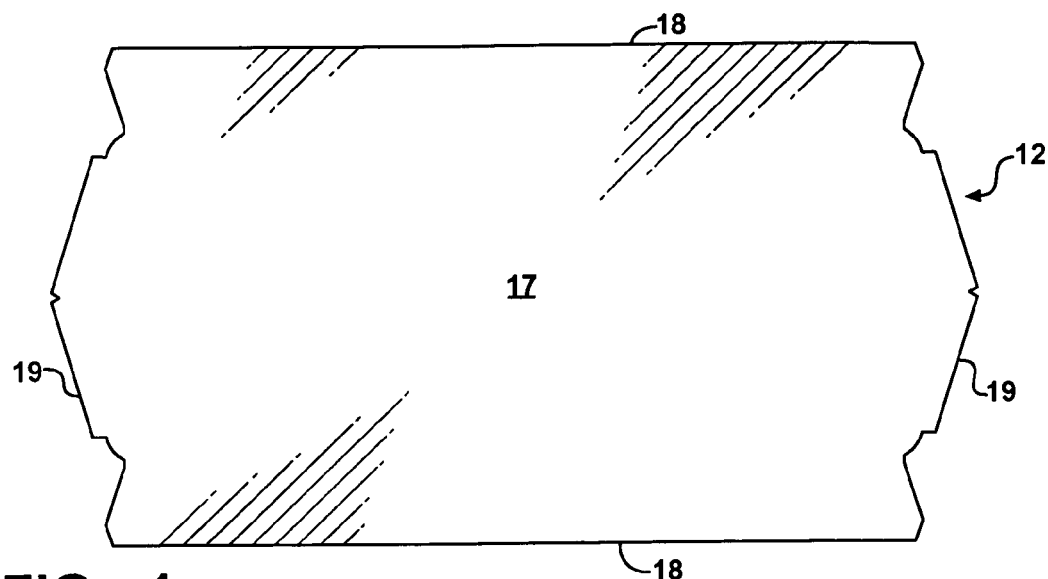
FIG. 1 is a top plan view of an upper sheet.

A sheet assembly constructed in accordance with the preferred embodiment is adapted for use with a patient support 1 (FIGS. 6 and 7) having a frame 2 composed of parallel, spaced rails 3 joined at corresponding ends by cross bars 4 equipped with wheels 5. The frame 2 mounts vertically adjustable uprights 6 provided at their upper ends with supports 7 which mount a patient supporting table 8 of such length and width as to enable a patient to be supported in supine position. The supports 7 are pivotable about a horizontal axis by means of a pivot pin 9, thereby enabling the opposite ends of the patient's support 8 to occupy different vertical levels.

The patient support 1 is intended to be illustrative of any one of a number of different kinds of patient supports. It can be a gurney, a trolley, an operating table, part of a radiologic imaging table, or any other appropriate support of the kind used for supporting and/or transporting a patient.

Figure 2:
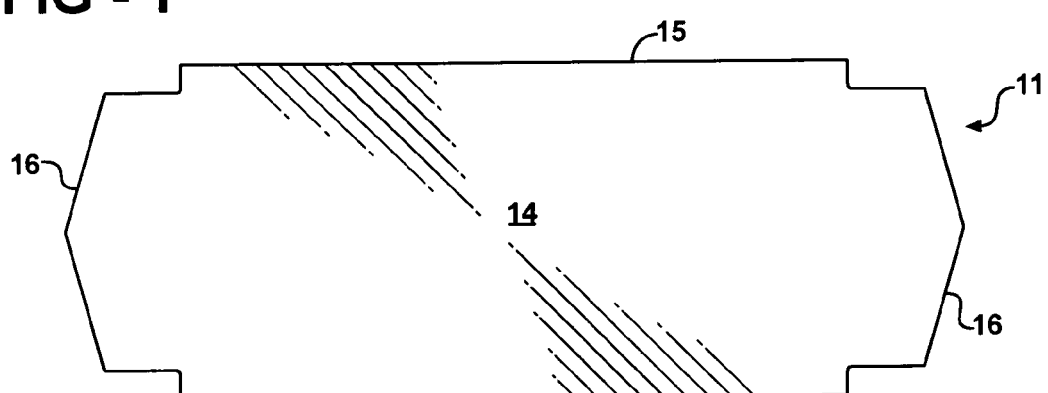
FIG. 2 is a top plan view of a lower sheet.
Figure 4:
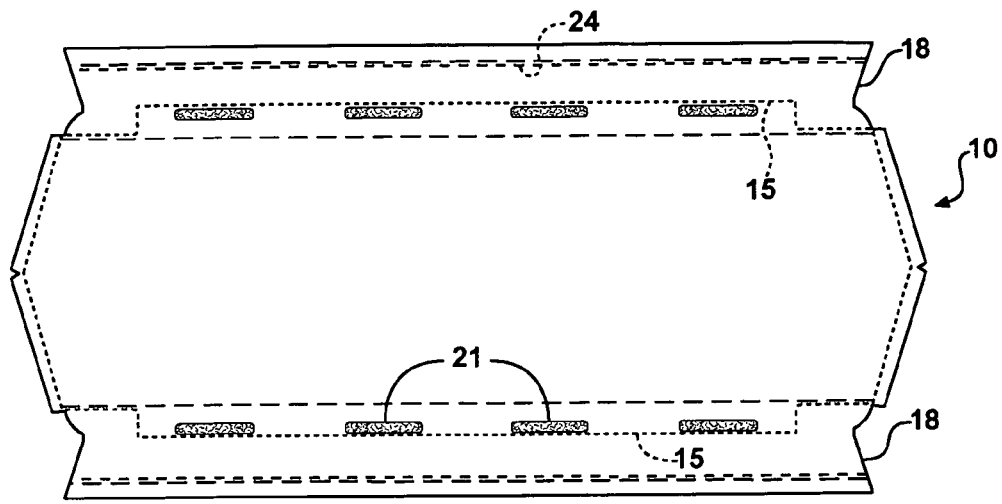
FIG. 4 is a top plan view of an assembled sheet assembly wherein the lower sheet is fitted with releasable securing strips and the free ends of the upper sheet are hemmed to form longitudinally extending pockets.

A sheet assembly constructed in accordance with the disclosed embodiment of the invention is indicated generally at 10 in FIG. 4 and comprises a bottom sheet 11 (FIG. 2) and an upper sheet 12 (FIG. 1) overlying the bottom sheet. The material from which the sheets is formed is a pliable, waterproof, durable plastic sheet of sufficient thickness to have the necessary strength to restrain a patient from falling off the support. The material from which the sheets are formed also has good radiolucency characteristics and is of substantially uniform thickness so as to have minimal density gradients. Plastic materials having these characteristics are well known and include polyethylene and polyvinylchloride of 8-10 mil thickness.

The two overlying sheets are secured to one another in any suitable manner. The securing of the upper and lower sheets to one another is inward from their side edges as is indicated by the dash lines 13 in FIG. 3 which represent the juncture.

The bottom or lower sheet 11 has a central planar patient supporting section 14 and an integral flap 15 at each of its two opposite sides. The lower sheet also has a longitudinally extending flap 16 at each of its opposite ends.

The upper sheet 12 has a central planar patient supporting section 17 of such width as to have an integral flap 18 at each of its opposite sides and an integral end flap 19 at each of its opposite ends.

The upper sheet 12 has a greater area than that of the lower sheet 11 so that, when the upper sheet is placed in overlying relation to the lower sheet, the flaps 18 of the upper sheet extend well beyond the flaps 15 of the lower sheet. The end flaps 19 of the upper sheet also extend beyond the end flaps 16 of the lower sheet.

Figure 3:
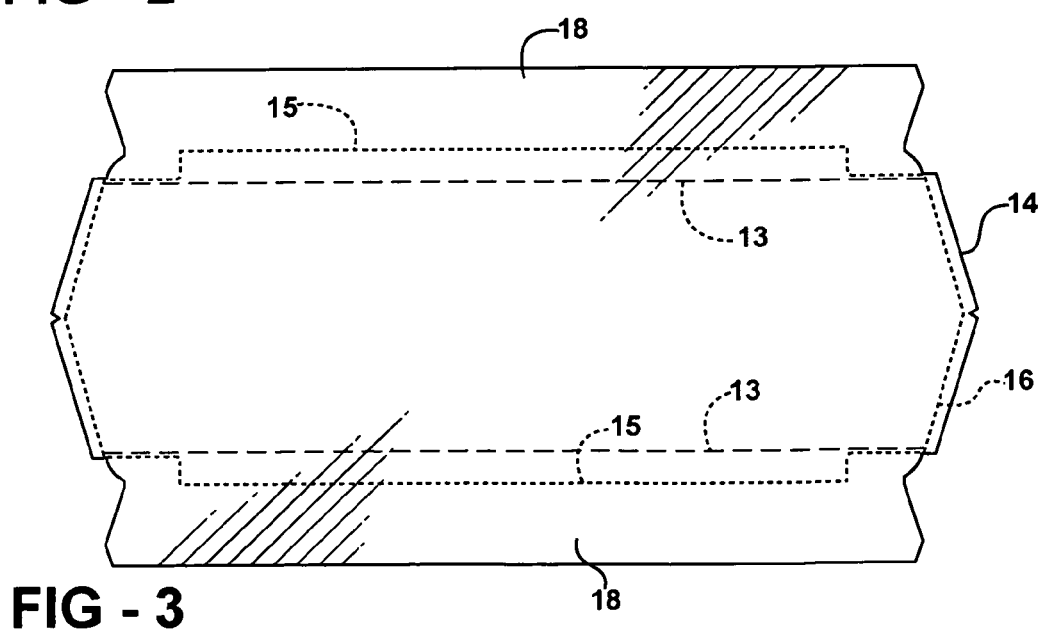
FIG. 3 is a top plan view of the upper and lower sheets in assembled, overlying relation.

Following placing of the two sheets in overlying position as is shown in FIG. 3, the two sheets may be joined to one another inwardly of their marginal side edges by heat sealing or in any other appropriate way. When the sheets are assembled, both pairs of flaps 15 and 18 are completely free of one another, thereby enabling the flaps 15 and 18 to be movable from a position in which they confront and overlie one another to a position in which they diverge.

Securing the two sheets to one another in the manner described enables the planar central sections 14 and 17 to form a receptacle therebetween for the accommodation of a cushioning pad (not shown), thereby providing a more comfortable support for a patient. The end flaps 16 and 19 may be heat sealed or otherwise secured to one another, if desired, thereby making it unnecessary to coat the pad with a cleanable coating and preventing contamination of the receptacle and the pad by the entrance of any fluid through either end of the assembly.

Figure 5:
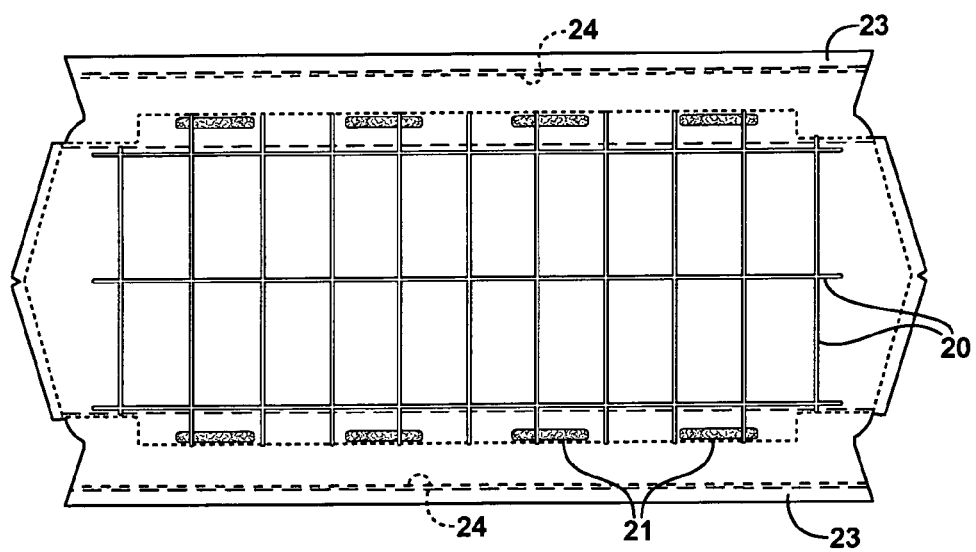
FIG. 5 is a view similar to FIG. 4, but illustrating the inclusion of indicia.
Figure 8:
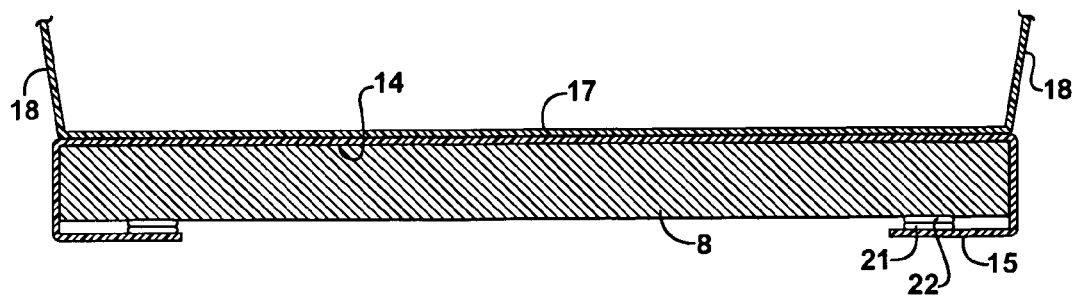
FIG. 8 is an enlarged sectional view taken on the line 8-8 of FIG. 6.

The sheets 11 and 12 may be opaque, translucent, transparent, or any combination thereof. If the upper sheet 12 is formed of transparent or translucent material, however, the lower sheet 11 or the cushioning pad, if used, may have indicia 20 (FIG. 5) thereon, which may be of assistance in performing a procedure on the patient.

The bottom sheet 11 has separable securing means 21 on its lower surface and adjacent the marginal edges of the flaps for the purpose of separably securing the sheet assembly atop a patient supporting table. As shown, the securing means 20 comprises the hook or loop section of a two-section fastener, the other section being secured to the lower surface of the patient support 8. The disclosed securing means can take other forms, such as grippers, snaps, releasable adhesives, or any other substitute securing means.

The flaps 18 of the upper sheet 12 have elongate pockets 23 at their marginal edges. Such pockets may be formed by reversely turning the marginal edge of each flap and heat sealing or otherwise hemming the free edge to the flap as is indicated by the dash lines 24.

Inserted in each of the pockets 23 is a coupling or retaining rod 25 of such length as to extend beyond both ends of the associated flap 18. Secured to each end of the rod 25 is a coupling enlargement 26. Each rod and enlargement are formed of a known rigid, plastic material which does not affect radiologic imaging.

In the disclosed embodiment the patient support 1 has at each of its opposite ends anchor means 27 comprising an upstanding anchor arm 28 to which is pivoted an anchor finger 29 having a slot 30 at its free end. The slot is of such width as to accommodate one end of the retaining rod 25, but will not accommodate the enlargement 25. Preferably, the arm 28 is provided with a cavity 31 for the accommodation of the finger 29 when the apparatus is not in use. No finger 29 can be pivoted from the extended position shown in FIGS. 6 and 7 toward the arm 28 at the opposite end of the patient support. The arm 28 also may be pivoted to the support 8 as long as its movement in a direction toward the opposite end of the support is limited.

In the operation of the apparatus a sheet assembly 10 is placed atop the upper surface of the support 8 with the bottom sheet 11 lowermost and the central planar sections 14 and 17 centered on the upper surface. The flaps 15 extend beyond opposite sides of the upper surface and may be turned under the marginal edges of the support 8 so that the fastener parts 21 and 22 confront and engage one another and secure the sheet assembly to the support. A patient then may be placed atop the sheet assembly.

Figure 6:
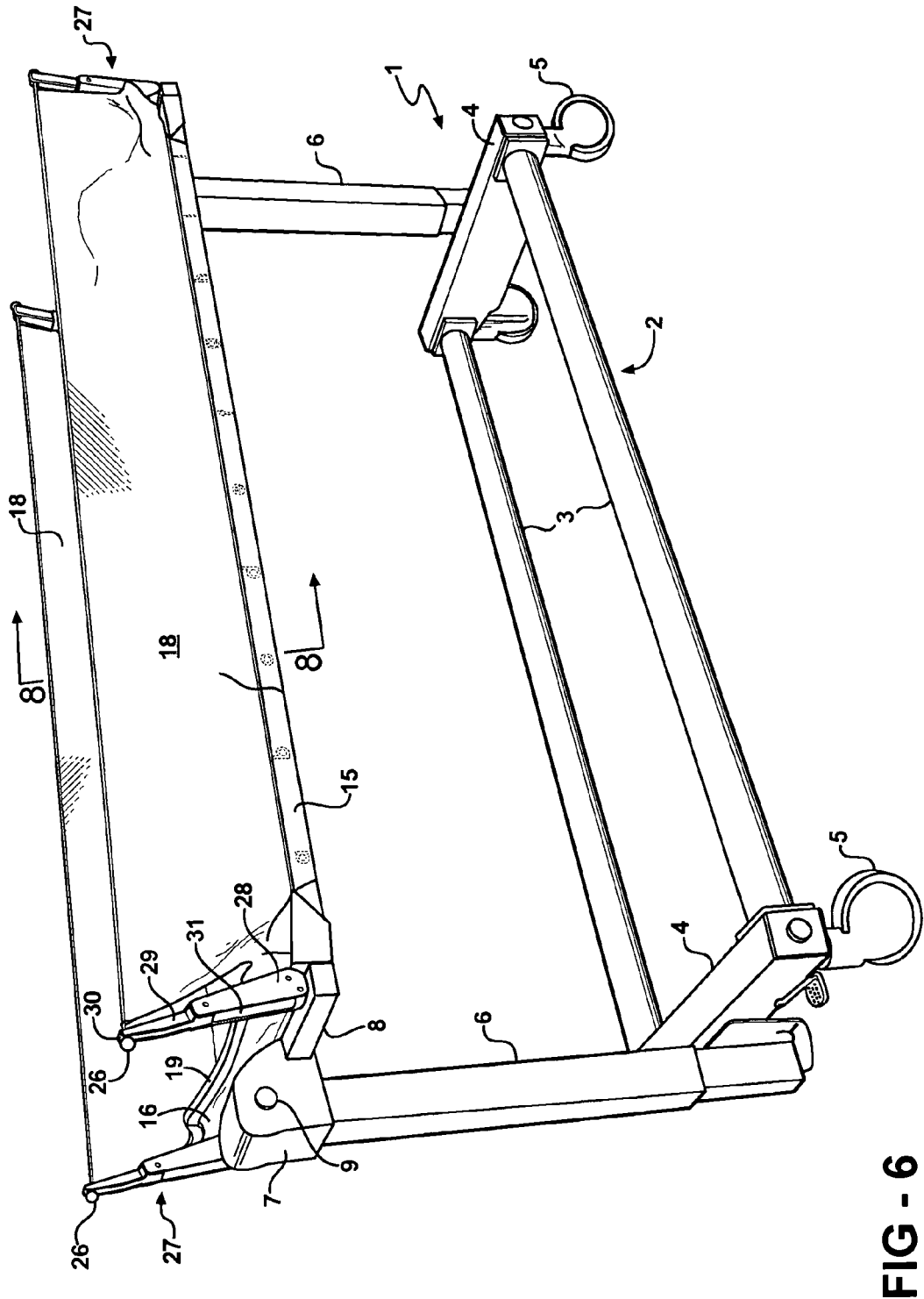
FIG. 6 is an isometric view illustrating the sheet assembly applied to the upper surface of a patient's support.
Figure 7:
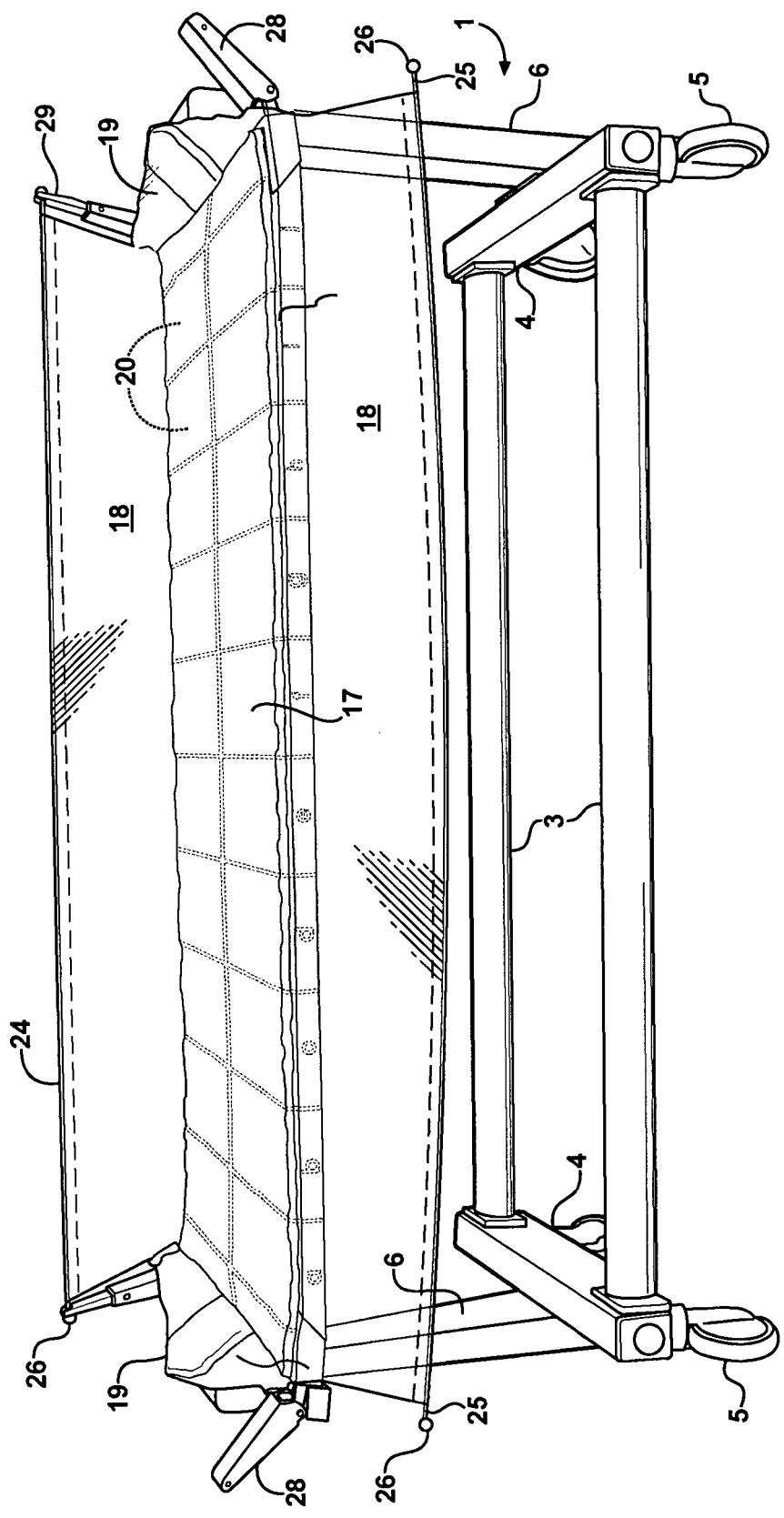
FIG. 7 is a view similar to FIG. 6, but illustrating one restraining flap in an upright position and a second restraining flap in a downwardly extending position.

If desired, either or both of the restraining flaps 18 may be raised and the adjacent anchor arms 28 elevated and the fingers 29 extended. The opposite ends of the retaining rod 25 may be fitted into the adjacent slot 30 with the enlargements 26 outboard of the fingers 29. The restraining flaps 18 thus will be in an elevated position relative to the patient support surface of the support 8 so as to restrain a patient from falling off the patient support. FIG. 6 shows both restraining flaps in raised positions, whereas FIG. 7 shows only one flap 18 elevated. The other flap 18 may simply occupy its lower, inactive position, thereby providing unrestricted access to a patient on the patient support.

When either or both of the restraining flaps are elevated, the opposite ends 16 and 19 of the lower and upper sheets also will be elevated to some extent, as is best shown in FIG. 7, thereby providing a barrier to the flow of fluids from opposite ends of the sheet assembly. The flaps 18, when elevated, not only function to restrain a patient, but also provide a barrier to the flow of fluids laterally off the patient support.

Because of the pliable nature of the material forming the sheet assembly the flaps 18 can accommodate projections such as those associated with backboards and splints, as well as braces and casts which may be worn by a patient. However, none of the materials from which the sheet assembly is formed have any adverse effect on imaging procedures which may be utilized in the examination or treatment of a patient.

The disclosed embodiment is representative of a presently preferred form of the invention, but is intended to be illustrative rather than definitive thereof. The invention is defined in the claims.

What is claimed is:

1. A sheet assembly for use with a patient support having opposite ends and opposite side edges and forming a support surface having longitudinal and transverse dimensions, said assembly comprising a lower sheet having a selected longitudinal dimension and a transverse dimension greater than that of said support surface whereby when said lower sheet is placed on said support surface opposite transverse sides of said sheet may form lower flaps having marginal edges extending beyond said opposite edges of said support surface and longitudinally of said support; an upper sheet overlying said lower sheet, said upper sheet having a selected longitudinal dimension and a transverse dimension greater than that of said support surface whereby opposite transverse sides of said upper sheet form upper flaps extending longitudinally of said support, said upper flaps having marginal edges and overlying said lower flaps; means fixing said upper and lower sheets to one another inward from the marginal edges of the respective flaps whereby the upper and lower flaps are free from one another; coupling means carried by said upper flaps for coupling said upper flaps to said support at a level above that of said support surface, said coupling means comprising a pocket adjacent the marginal edge of each of said upper flaps and a rod carried in said pocket and extending beyond opposite ends of said pocket; and upstanding anchor bars carried by said support adjacent opposite ends of said rod, each of said anchor bars having an opening therein for the accommodation of said rod.

2. The assembly according to claim 1 including an enlargement at each end of said rod.

3. The assembly according to claim 1 wherein the enlargement at opposite ends of each of said rods is larger than the opening in each of said anchor bars.

4. The combination of a sheet assembly and a person support member, said support member having an upper support surface, said support surface having length and width dimensions, said sheet assembly overlying said support surface and comprising a lower sheet and an upper sheet overlying said lower sheet, each of said sheets having a length dimension extending longitudinally of said support surface and a width dimension greater than that of said support surface whereby opposite sides of said lower and upper sheets extend beyond opposite sides of said support surface and form lower and upper flaps respectively; securing means carried by said lower sheet and securing said lower sheet to said support member, said upper sheet having a width dimension greater than that of said lower sheet whereby said upper flaps overlie and extend beyond said lower flaps; means securing said upper and lower sheets to one another inward of said lower and upper flaps whereby said upper flaps overlie said lower flaps but are free therefrom; anchor means carried by said support adjacent said opposite sides of said support surface and extending upward to a level above that of said support surface; and coupling means carried by said upper flaps and engageable with said anchor means for supporting and maintaining said upper flaps in an elevated position above said upper surface and in which said upper flaps form a safeguard against a person's falling off said support surface, said anchor means having openings therein and wherein said coupling means includes rigid rods carried by said upper flaps and accommodated in the openings of said anchor means.

5. The combination according to claim 4 wherein said rods have enlargements at their ends of such size as to be incapable of passing through said openings.

6. The combination according to claim 4 wherein said securing means comprises first means carried by said lower flaps and second means carried by said support member and engaged with said first means.

7. The combination according to claim 4 wherein each of said sheets is formed of pliable material having a low density gradient.

8. The combination according to claim 4 wherein at least one of said sheets is formed of waterproof material.

9. The combination according to claim 4 wherein at least said upper sheet is formed of translucent material.

* * * * *